(12) United States Patent
Gulliver et al.

(10) Patent No.: US 10,463,826 B2
(45) Date of Patent: Nov. 5, 2019

(54) HEADGEAR, INTERFACE AND AN ASSEMBLY

(71) Applicant: Fisher & Paykel Healthcare Limited, Auckland (NZ)

(72) Inventors: Laurence Gulliver, Auckland (NZ); Michael Paul Ronayne, Auckland (NZ); Charles William Douglas Irving, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 1213 days.

(21) Appl. No.: 14/401,446

(22) PCT Filed: May 15, 2013

(86) PCT No.: PCT/NZ2013/000082
§ 371 (c)(1),
(2) Date: Nov. 14, 2014

(87) PCT Pub. No.: WO2013/172719
PCT Pub. Date: Nov. 21, 2013

(65) Prior Publication Data
US 2015/0075534 A1 Mar. 19, 2015

Related U.S. Application Data

(60) Provisional application No. 61/648,013, filed on May 16, 2012.

(51) Int. Cl.
*A61M 16/06* (2006.01)
*A42B 3/08* (2006.01)

(52) U.S. Cl.
CPC .......... *A61M 16/0683* (2013.01); *A42B 3/08* (2013.01); *A61M 16/0605* (2014.02); *A61M 16/0688* (2014.02); *A61M 2240/00* (2013.01)

(58) Field of Classification Search
CPC .......... A61M 16/0683; A61M 2240/00; A61M 16/0688; A42B 3/08
(Continued)

(56) References Cited

U.S. PATENT DOCUMENTS 3,551,911 A * 1/1971 Holden .................... A42B 3/00
2/411
5,269,296 A 12/1993 Landis
(Continued)

FOREIGN PATENT DOCUMENTS

EP 0747078 A2 12/1996

OTHER PUBLICATIONS

European Examination Report; dated Feb. 20, 2017, 4 pages.
(Continued)

*Primary Examiner* — Tan-Uyen T Ho
*Assistant Examiner* — Victoria Murphy
(74) *Attorney, Agent, or Firm* — Knobbe, Martens, Olson & Bear, LLP

(57) ABSTRACT

This invention relates to a headgear component as a part of a headgear. The component comprising a backstrap, a first ear loop extending from one end of the backstrap, the first ear loop following a path defining a first ear opening, and a second ear loop extending from another end of the backstrap, the second ear loop following a path defining a second ear opening. A first pair of connection zones is on the first ear loop, each connection zone spaced an equal distance from the backstrap and spaced from each other, and a second pair of connection zones on the second ear loop, each connection zone spaced an equal distance apart from the backstrap and spaced from each other. A connection zone of the first pair and a connection zone of the second pair are on a first side of the backstrap, and a connection zone of the first pair and a connection zone of the second pair are on a second
(Continued)

(other) side of the backstrap, wherein the headgear component is substantially of a symmetrical shape.

20 Claims, 10 Drawing Sheets

(58) Field of Classification Search
USPC .................................................. 128/207.11
See application file for complete search history.

(56) References Cited

U.S. PATENT DOCUMENTS

| | | | | |
|---|---|---|---|---|
| 5,361,420 | A | * | 11/1994 | Dobbs .................... A42B 1/068 2/421 |
| 5,517,986 | A | | 5/1996 | Starr et al. |
| 5,685,021 | A | | 11/1997 | Tsujino |
| 5,724,965 | A | * | 3/1998 | Handke ................. A61M 16/06 128/205.25 |
| 6,470,886 | B1 | * | 10/2002 | Jestrabek-Hart ............................ A61M 16/0683 128/207.11 |
| 7,296,575 | B1 | | 11/2007 | Radney |
| 2007/0062462 | A1 | * | 3/2007 | McGuire .............. A01K 13/006 119/850 |
| 2008/0060649 | A1 | * | 3/2008 | Veliss ................... A61M 16/06 128/205.25 |
| 2009/0250065 | A1 | | 10/2009 | Omura et al. |
| 2011/0072553 | A1 | | 3/2011 | Ho |
| 2011/0265796 | A1 | * | 11/2011 | Amarasinghe ........ A61M 16/06 128/206.28 |

OTHER PUBLICATIONS

Australian Examination Report; dated Mar. 18, 2017; 4 pages.
European Search Report; dated Dec. 17, 2015; 8 pages.
International Search Report and Written Opinion; PCT/NZ2013/000082; dated Jul. 23, 2013; 9 pages.
European Examination Report; dated Aug. 30, 2018, 6 pages.
Australian Examination Report; dated Mar. 7, 2019, 3 pages.

* cited by examiner

HEADGEAR, INTERFACE AND AN ASSEMBLY

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

FIELD OF THE INVENTION

The present invention generally relates to components for medical systems for conveying gases to and/or from a patient. In one particular aspect, the invention relates to headgear, a patient interface, or an assembly of headgear and a patient interface as part of a medical system for conveying breathable gases to and/or from a patient or as part of a breathing system.

BACKGROUND OF THE INVENTION

Alternative and improved retention systems for positioning, such as fixed positioning, of gas delivery interface systems, such as masks, nasal cannula or other oronasal gas delivery interface units, for a user of the interface are always being sought.

Typically, in infant applications, due to the size of the head of the infant, adhesive patches or other dermal connection systems are used to position such gas delivery interfaces. For example, adhesive tape is applied over the tube or part of a nasal cannula to hold the cannula in place or an operation position on the infant's face. This causes a number of problems, such as skin reactions, skin abrasion, or breakdown when tape is repeatedly applied and removed, especially when an infant is being cycled between different types of gas therapy.

Many complex systems, including elasticised straps, buckles, tensioners, and other such retaining systems, are utilised in holding or positioning of user interfaces on the face or in preferred installation positions on a user. Therefore, a system for improved ease of application or installation of such interfaces to a user, such as by the user or by a carer of the user are desirable. Ease of being able to cycle between different treatment therapies would also be desirable, especially also reducing the need for handling of a user's head or applying and re-applying adhesives, glues, or tapes to the face of the user for positioning of a gas delivery interface in an operational position.

Further, stresses applied to the head of a user from various complex headgears may result in stress sores or contact abrasion. Therefore, minimising the overall stresses applied to the head of a user is also desirable. Stresses applied to the head or face of a user, depending on where tension is exerted from such more complex headgear arrangements, can sometimes result in "snub nosing". The likelihood of snub nosing preferably is reduced or eliminated.

In this specification, any references to other patent specifications, other external documents, or other sources of information are generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

Further aspects and advantages of the present invention will become apparent from the ensuing description, which is given by way of example only.

SUMMARY OF THE INVENTION

It is therefore an object of the present invention to provide a headgear and/or an interface, or an assembly of both a headgear and an interface, which will go at least some way towards addressing the foregoing problems or which will at least provide the public with a useful choice.

In a first aspect, the present invention may broadly comprise a headgear comprising a semi-rigid frame engageable with the head of a user, and a releasable connection system for releasable connection with a user interface.

In a further aspect, the present invention may broadly comprise a headgear comprising
a semi-rigid frame engageable with the head of a user,
a releasable connection system for releasable connection with a user interface, wherein
the frame extends generally about a rear region of a user's head, generally about an upper region of a user's head, and generally about an ear or both ears of a user.

In one embodiment the releasable connection system may be provided on or about a region of the frame extending generally about the ear or ears of the user. In another embodiment the releasable connection system may be provided on or about a region of the frame extending generally in front of the ear or ears of the user. In another embodiment the releasable connection system may be provided as a region at or in front of the ear or ears of a user.

Preferably the releasable connection system may be a two-part connector system. More preferably, a first connector part or portion may be provided by, or on, a region of the headgear, and a second connector part or portion may be provided by, or on, a region of (or in attachment or connection with) a user interface.

In one embodiment the first connector part or portion is one of a hook or a loop of a hook and loop type fastener system, and the second connector part or portion is the other of a loop or a hook for the hook and loop type fastener system.

In another embodiment the two-part connector system is a system of magnets. Preferably the first connector part or portion is a first magnet or series of magnets, and the second connector part or portion is the other or a second magnet or series of magnets (e.g. such as a magnet or magnets of opposite polarity to the first magnet or series of magnets).

In another embodiment, the two-part connector system is a snap-dome connection system.

In another embodiment, the two-part connector system may be provided by a two-part adhesive, where the first connector part or portion is provided with an adhesive that is receivable by the second part or portion, or where the second connector part or portion is provided with an adhesive that is receivable by the first part or portion, or where the first part or portion provides for the first of a two-part adhesive, and the second part or portion provides for the second of a two-part adhesive, whereby the bringing together of the first and second parts or portions facilitates or enables adhesion between the two parts. Advantageously, the parts are releasably adherable to each other.

Preferably the first part comprises an adhesive and the second part is receivable of the adhesive or bondable with the adhesive, or the second part comprises an adhesive and the first part is receivable of the adhesive or bondable with the adhesive, or both the first and second parts comprise an adhesive or one part of a two-part adhesive. Optionally, such an adhesive is a releasable adhesive system, or is a non-permanent binding or bonding together of adhesive or adhesive receiver parts.

Preferably, the user interface may be a gas delivery system or a gas delivery device. More preferably the user interface may be a device for supplying of breathable gas to a user. Preferably the user interface may be any one or any combination of: mask, nasal cannula, oronasal device. Preferably the interface may be connectable to a breathing tube.

In one embodiment the releasable connection system may be of a substantially low or flat profile. In another embodiment the releasable connection system may be of a substantially similar profile to the profile of the frame. Preferably the profile is generally substantially planar or substantially flat (for example, may be planar or flat in profile).

Preferably the releasable connection system may be an interference attachment system. More preferably the interference attachment system provides for connection or connectability between a user interface (or a part thereof, or a part connected or attached to a user interface) and one or more of:

the headgear region extending generally about the ear or ears of a user, the headgear region extending generally in front of the ear or ears of a user, the headgear region at or in front of the ear or ears of a user.

Preferably the interference attachment system may be a two-part connector system as defined above.

In one preferred embodiment, advantageously, the releasable connection system does not utilise pulley strap systems or buckles. Pulley or buckle type systems can impact on a user's face, particularly an infant face. For example, application of a connection or retention system too tightly on a user's face may contribute to so-called "snub nosing", such as when forces are applied to the nose, septum or philtrum.

Preferably the releasable connection system enables connection between a user interface and the headgear, whilst reducing the likelihood of the application of tension during installation of the user interface to a user in combination with the headgear.

Preferably the releasable connection system reduces the likelihood of the need for application of adhesive, or adhesive tape, to a user's skin for the installation and placement of a user interface into an operational position, or may reduce the likelihood of the application of adhesive to a user's skin in installation or adhesive applied to a user's skin for connection of a user interface.

Preferably the frame extending generally about the ears of the user may partially or wholly surround or encircle one or both ears. More preferably the frame extending about the ear or ears of a user is a loop about an, or each, ear of the user.

Preferably the headgear may be adjustable.

Preferably the headgear may be provided in a ready-to-receive mode for receiving the head of a user and/or connecting with or connectable to/with a user interface (or a part or portion thereof).

Preferably the headgear may be provided in a ready-to-receive mode for receiving a user interface (or a part of a portion thereof).

Preferably the headgear may be adjustable for fitment to a user's head, such as for anatomical adjustment.

Preferably the headgear may be adjustable for different user head sizes.

Preferably the headgear may be adjustable for varying the distance the frame extends between the rear region (or region above the nape of a user's neck) and the portion of the frame that extends generally about the ear or ears of a user.

Preferably the headgear may be adjustable for varying the distance the frame extends between the upper region (or top) of a user's head and the portion of the frame that extends generally about the ear of ears of a user.

Preferably the frame extending generally about the ear or ears of a user may be adjustable, more preferably the loop about an, or each ear of the user, may be adjustable, such as adjustable by the size of the loop provided for encircling partially or wholly the ear or ears of a user.

Preferably the frame may include an adjustment strap or straps. Preferably the adjustment strap or one of the adjustment straps may be a part of the frame positionable generally about the upper region (or top) of the user's head. Alternatively the adjustment strap or one of the adjustment straps may be a part of the frame positionable generally about the rear region (or region above the nape of the user's neck). More preferably the adjustment straps may be both a part of the frame positionable generally about the upper region (or top) of the user's head and the frame positionable generally about the rear region (or above the nape region of the user's neck).

Preferably the adjustment strap or straps may be of a hook and loop type fastener system for adjustable fastening. More preferably, or alternatively, the adjustment strap or straps comprise or include a buckle arrangement, where an adjustment strap is insertable through a buckle.

Preferably the rear region may be a lower rear region of the user's head. More preferably the rear region may be a region above the nape of the user's neck.

Preferably the upper region may be a region about the top of a user's head.

Preferably the frame is formed of or from a semi-rigid material.

Preferably the frame is of a self-sustaining shape.

Preferably the frame is supportive of an interface which may be connected thereto.

Preferably the frame is provided as one-piece or as a single part article or is a unitary piece of headgear. For example, the frame preferably is not provided by multiple straps or multiple parts that must be assembled or connected together to provide the semi-rigid headgear.

Preferably the semi-rigid frame may be of a substantially non-elastic construction or substantially non-elastic material.

Preferably the frame may be of a substantially self-supporting shape and/or configuration.

Preferably the frame forms a semi-rigid frame about the head of a user.

Preferably the frame is supportive of an interface which may be connected thereto.

Preferably the frame provides a substantially self-supporting frame to which a user interface (or a part thereof, or a part connected or attached to a user interface) may be connectable and supported in-situ therefrom.

Preferably the releasable connection system may be capable of supporting shear and/or pull forces that may be imparted from connection of a user interface.

Preferably the frame may be of a substantially planar or substantially flat profile, the planar or flat profile generally contoured for planar or flat contact with a user's head.

Preferably the frame may be of a non-frayable woven material or fabric.

Preferably the frame may be of a non-woven material or fabric, alternatively may be of a semi-rigid polymer.

Preferably the frame may be formed of a thermoplastic or thermosetting polymeric material or composites therefrom. Alternatively, the frame may be formed of or from a weldable polymeric material.

Preferably the frame may be formed from a polyethylene terephthalate (PET), a polyethylene (PE), or polyester.

Preferably the frame may be formed from a non-woven polyethylene terephthalate (PET)/polyethylene (PE) laminated composite, or a non-woven PET/polyester laminated composite.

Preferably the headgear, or user interface, or both, are for an infant. More preferably, the headgear, or user interface, or both, are sized or designed for an infant.

In a further aspect, the present invention may broadly comprise a user interface comprising adapted for use with the headgear of the above aspects.

In a further aspect, the present invention may broadly comprise a user interface of the above aspect comprising:
 a user interfacing part or portion, and
 releasable connection system part or portion for releasable connection with a headgear connectable part or portion.

Preferably the releasable connection system part of portion may be provided by, or on, a region of (or in attachment or connection with) the user interface.

Preferably the releasable connection system part or portion may be integral with the user interfacing part or portion or may be over-moulded with the user interfacing part or portion.

Preferably the releasable connection system may form a backing or a substrate to which the user interface is attached or connected or connectable thereto.

Preferably, the user interface is provided with one or a pair (or more) of parts or portions connectable with the headgear. More preferably, a pair of parts or portions extend from a user interface for connection with the headgear.

Preferably the headgear connectable part or portion is substantially non-elastic.

Preferably the releasable connection system part or portion forms one part of a two-part connection system. More preferably the other of the two-part connection system may be provided by the frame (or headgear) ad defined above.

Preferably the releasable connection system may be a strip or a strap or a length of a connector part of the connection system. More preferably the strip or strap or length extends to be connectable to, or on, or about a region of, the frame (or headgear) as defined above.

As discussed above, in one preferred embodiment, advantageously, the releasable connection system does not utilise pulley strap systems or buckles. Pulley or buckle type systems can impact on a user's face, particularly an infant face. For example, application of a connection or retention system too tightly on a user's face may contribute to so-called "snub nosing", such as when forces are applied to the nose, septum or philtrum.

Preferably the releasable connection system enables connection between a user interface and the headgear, whilst reducing the likelihood of the application of tension during installation of the user interface to a user in combination with the headgear.

Preferably, a first connector portion may be provided by, or on, a region of headgear (as defined above), and a second connector portion may be provided by, or on, a region of (or in attachment or connection with) the user interface.

In one embodiment the releasable connection system part or portion of the user interface may be of a substantially low profile. In another embodiment the releasable connection system part of portion of the user interface may be of a substantially similar profile to the profile of the frame. Preferably the profile is generally substantially planar or substantially flat (e.g. in profile).

Preferably the releasable connection system part or portion of the user interface may be an interference attachment system. More preferably the interference attachment system part or portion provides for connection or connectability between the user interface (or a part thereof, or a part connected or attached to a user interface) and one or more of:
 the headgear region extending generally about the ear or ears of a user,
 the headgear region extending generally in front of the ear or ears of a user,
 the headgear region at or in front of the ear or ears of a user.

Preferably the interference attachment system may be a two-part connector system as defined above.

Preferably, the user interface may be a gas delivery system or a gas delivery device. More preferably the user interface may be a device for supplying of breathable gas to a user. Preferably the user interface may be any one or any combination of: mask, nasal cannula, oronasal device.

Preferably the user interface is held in a substantially fixed or operational position when in connection with the headgear.

Preferably the user interface is held in a substantially secure fixed or operational position when in connection with the headgear.

Preferably the interface may be connectable to a breathing tube.

Preferably the headgear, or user interface, or both, are for an infant. More preferably, the headgear, or user interface, or both, are sized or designed for an infant.

In a further aspect, the present invention may broadly comprise an assembly comprising:
 a headgear, the headgear as defined above, and
 a user interface, the user interface as defined above,
 the headgear and user interface releasably connectable to each other.

Preferably the headgear is supportive of the user interface in an in-situ or installed in-use position with or on a user of the interface.

Preferably the headgear may comprise a first part of a two-part releasable connection system, and the user interface or a region of (or in attachment or connection with) the user interface comprises a second of the two-part releasable connection system. More preferably, the first and second parts may be releasably connectable for retaining of the interface in a user in-use position, or configuration.

In one embodiment the first part is one of a hook or a loop of a hook and loop type fastener system, and the second part is the other of a loop or a hook for the hook and loop type fastener system.

In another embodiment the two-part connector system is a system of magnets. Preferably the first connector part or portion is a first magnet or series of magnets, and the second connector part or portion is the other or a second magnet or series of magnets (e.g. such as magnets of opposite polarity to the first magnet or series of magnets).

In another embodiment, the two-part connector system may be provided by a two-part adhesive, where the first connector part or portion is provided with an adhesive that is receivable by the second part or portion, or where the second connector part or portion is provided with an adhesive that is receivable by the first part or portion, or where the first part or portion provides for the first of a two-part adhesive, and the second part or portion provides for the second of a two-part adhesive, whereby the bringing together of the first and second parts or portions facilitates or enables adhesion between the two parts. Advantageously, the parts are releasably adherable to each other.

Preferably the first part comprises an adhesive and the second part is receivable of the adhesive or bondable with the adhesive, or the second part comprises an adhesive and the first part is receivable of the adhesive or bondable with the adhesive, or the both the first and second parts comprises an adhesive or one part of a two-part adhesive. Optionally, such an adhesive is a releasable adhesive system, or is a non-permanent binding or bonding together of adhesive or adhesive receiver parts.

Preferably the interface may be connectable to a breathing tube.

Preferably the headgear, or user interface, or both, are for an infant. More preferably, the headgear, or user interface, or both, are sized or designed for an infant.

The headgear and/or user interface of this invention may be utilised in combination or conjunction with any one or more of the inventions described in PCT/NZ2011/000218, the contents of which is herein incorporated by reference.

In yet a further aspect of the invention, there is provided a headgear component as a part of a headgear comprising:
a backstrap,
a first ear loop extending from one end of the backstrap, the first ear loop following a path defining a first ear opening,
a second ear loop extending from another end of the backstrap, the second ear loop following a path defining a second ear opening,
a first pair of connection zones on the first ear loop, each connection zone spaced an equal distance from the backstrap and spaced from each other,
a second pair of connection zones on the second ear loop, each connection zone spaced an equal distance apart from the backstrap and spaced from each other,
a connection zone of the first pair and a connection zone of the second pair are on a first side of the backstrap, and a connection zone of the first pair and a connection zone of the second pair are on a second (other) side of the backstrap, wherein the headgear component is substantially of a symmetrical shape.

Preferably the backstrap is adapted to cross behind the head below the occiput or occipital bone.

Preferably the headgear component is symmetrical along a first plane and a second plane.

Preferably the first plane corresponds with the sagittal plane of the user, and the second plane corresponds with the transverse plane of the user.

Preferably the headgear component is symmetrical along a third plane.

Preferably the third plane corresponds with the coronal plane of the user.

Preferably the headgear component is symmetrical about the backstrap.

Preferably each strap includes projecting portions, and the connection zones are located on the projecting portions.

Preferably the headgear component is a flat web of a material, the web being bendable but substantially non-extensible.

Preferably the headgear component is reversible so that each face of the web is of a material that may comfortably contact the user.

Preferably the headgear component is a flat web of a material, and each connection zone includes a component of a releasable fastening system on both the first and second sides of the web of material.

Preferably a top strap comprising a first end and second end, may have the first end releasably fastened to one of the first pair of connection zones presently outwardly, and the second end releasably fastened to one of the second pair of connection zones presented outwardly, the top strap extending substantially across an upper region or top of a user's head.

Preferably connection zones are provided on both faces of the headgear component.

Preferably the headgear component includes one or more rigidising members in the backstrap.

Preferably said rigidising member comprises one or more of copper wire, a copper piece or strap or strip, aluminium wire, aluminium piece or strap or strip, ductile or conformable plastics.

Preferably the shapes and relative positioning of the backstrap, the ear loops, and the connection zones, being such that in a first mode of use, the backstrap crosses behind the head below the occiput or occipital bone, an ear loop is disposed around each ear, the connection zones to the first side of the backstrap presenting outwardly from a user's head, and the connection zones on the second side of the backstrap presenting inwardly toward a user's head, and in a second mode of use, the backstrap crosses behind the head below the occiput or occipital bone, an ear loop is disposed around each ear, the connection zones to the second side of the backstrap presenting outwardly from a user's head, and the connection zones on the first side of the backstrap presenting inwardly toward a user's head.

Preferably one pair of the connection zones forms in use, a releasable connection system for releasable connection with a user interface.

Preferably the releasable connection system is a two-part connector system.

Preferably each connection zone includes a component of the two-part releasable connector system.

Preferably a first connector part or portion of the two-part connector system is one of a hook or a loop of a hook and loop type fastener system, and a second connector part or portion of the two-part connector system is the other of a loop or a hook for the hook and loop type fastener system.

Preferably a user interface is releasably connectable to the headgear component at the connection zones, said user interface being of a gas delivery device type.

Preferably the user interface is a device for supplying breathable gas to a user.

Preferably the user interface is any one or any combination of: mask, nasal cannula, oronasal device.

Preferably the user interface is connectable to a breathing tube.

Preferably the releasable connection system is of a substantially low or flat profile.

Preferably the releasable connection system is of a substantially similar profile to the profile of the frame.

Preferably the profile is generally substantially planar or substantially flat.

Preferably the releasable connection system is an interference attachment system.

Preferably the releasable connection system enables connection between a user interface and the headgear component, whilst reducing the likelihood of application of tension during installation of the user interface to a user in combination with the headgear.

Preferably the releasable connection system reduces the likelihood of the need for application of adhesive, or adhesive tape, to a user's skin for the installation and placement of a user interface into an operational position.

Preferably the headgear component is a provided as one-piece or as a single part article or is a unitary piece of headgear.

Preferably the component forms a part of a semi-rigid headgear frame is of a substantially non-elastic construction and/or substantially non-elastic material.

Preferably the frame is of a substantially planar or substantially flat profile, the planar or flat profile generally contoured for planar or flat contact with a user's head.

Preferably the headgear component, or user interface, or both, are for an infant.

Preferably the headgear component, or user interface, or both, are sized or designed for an infant.

In yet a further aspect there may be provided a user interface adapted for use with the headgear component as defined in the aspect above.

Preferably the headgear component of this aspect may be used as a part or forms a part of the headgear defined in any one of the aspects above.

For the purposes of this specification, reference to "semi-rigid" may be defined as the headgear (or frame) having a form generally maintained by a structure or by materials selected to generally maintain a pre-determined shape or configuration, or which is generally self-supporting of its own weight and of a shape or form produced or formed during manufacture, construction or assembly of parts. Such a definition of semi-rigid includes the ability of such material to form to be able to be manipulated into alternative shapes or forms by adjustment of the relative parts or pieces making up the shape or form being semi-rigid themselves.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

This invention may also be said broadly to be embodied in the parts, elements and features referred to or indicated in the specification of the application, individually or collectively, and any or all combinations of any two or more said parts, elements or features, and where specific integers are mentioned herein which have known equivalents in the art to which this invention relates, such known equivalents are deemed to be incorporated herein as if individually set forth.

The invention is embodied in the foregoing and also envisages constructions of which the following gives examples only.

BRIEF DESCRIPTION OF THE DRAWINGS

Preferred embodiments of the invention will be described by way of example only and with reference to the drawings, in which.

DETAILED DESCRIPTION OF THE INVENTION

Figure 1:
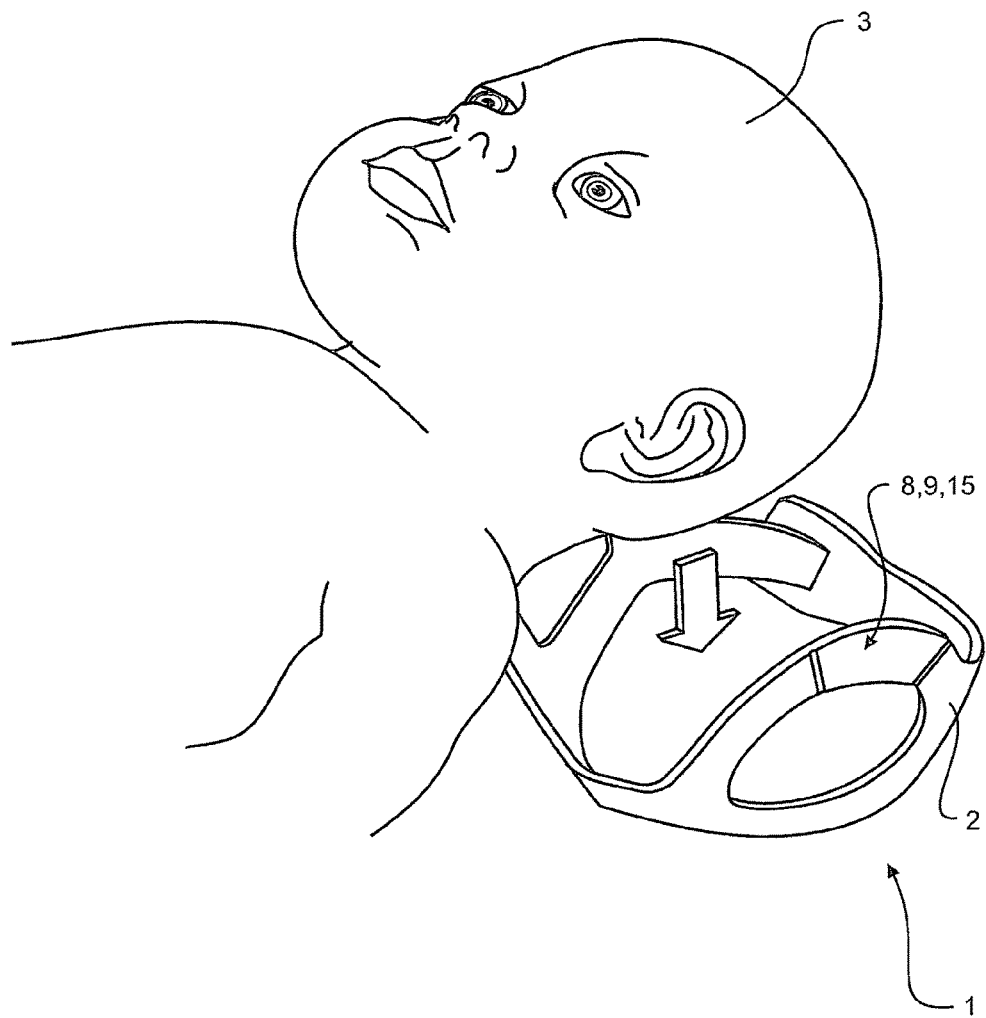
FIG. 1 shows a headgear according to one embodiment of the invention ready to receive the head of a user.

In one embodiment there is provided a headgear 1. Headgear 1 comprises a semi-rigid frame 2 engageable with the head 3 of a user, and a releasable connection system for releasable connection with a user interface 4.

The headgear 1 is easily and conveniently removable from, or installable on, the head 3 of a user. Advantageously, the semi-rigid nature of the headgear allows for resultant minimal handling of a user or user's head during installation of the headgear or installation of a user interface to a user to an operational position. Further, the present invention provides for improved security of maintaining the position of a user interface with a user (e.g. prongs remaining in position in the nares of a user's nose) from the inter-connection of the user interface with the headgear.

It should be appreciated there are a number of disadvantages and problems associated with the need for re-positioning of an interface, particularly an infant interface. Included is "snub nosing", epidermal abrasion, or dermal allergies from traditional tapes or their adhesives. Such problems are also incurred during the cycling of a user between different treatment options and, traditionally, the subsequent need to remove headgear or tapes or user interfaces and then the installation of new equipment and user interfaces or interface positioning headgear or other gear.

Therefore, provision of a headgear that is in a ready-to-receive mode for receiving of a user's head or the user interface (or both) is a useful step in progressing toward reducing the problems users have previously been faced with. Further, improving the ease of installation, both in terms of complexity as well as time and effort by a carer (e.g. nurse), is of further benefit.

In a further embodiment headgear 1 comprises a semi-rigid frame 2 engageable with the head 3 of a user. The frame 2 extends generally about a rear region 5 of a user's head 3, generally about an upper region 6 of a user's head 3, and generally about an ear 7 or both ears 7 of a user. Such a frame 2 further comprises a releasable connection system for releasable connection with a user interface 4.

The releasable connection system can be on or about a region of the frame extending generally about the ear or ears of the user, or can be provided on or about a region of the frame extending generally at or in front of the ear or ears of the user, such as the region indicated by reference numeral 8.

The releasable connection system can be a two-part connector system. For example, a first connector part or portion 9 may be provided by, or on, a region of the headgear, such as for example region 8. A second connector part or portion 10 may be provided by, or on, a region of (or in attachment or connection with) a user interface, such as the region indicated by reference numeral 11.

FIG. 1 shows a headgear 1 in a configuration which is ready to receive the head 3 of a user.

Figure 6:
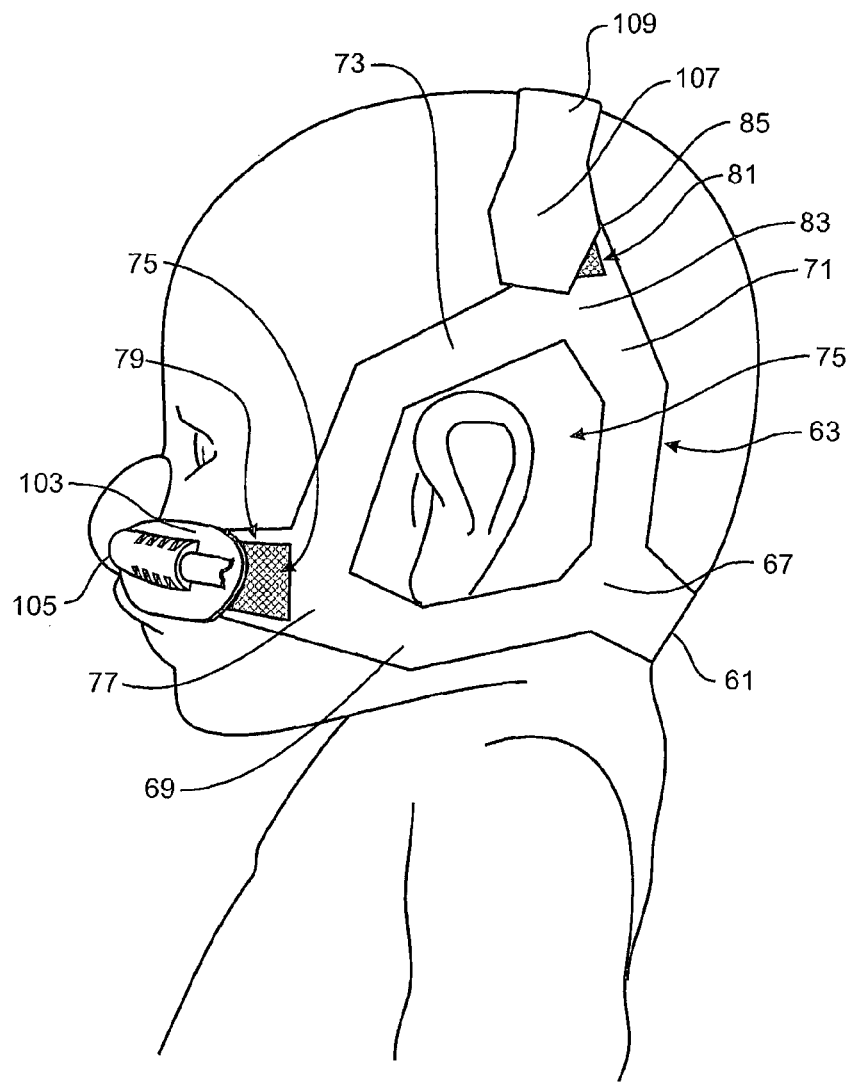
FIG. 6 is a profile view showing a headgear in position about the head of a user, with an interface connected and in position on the user.
Figure 6A:
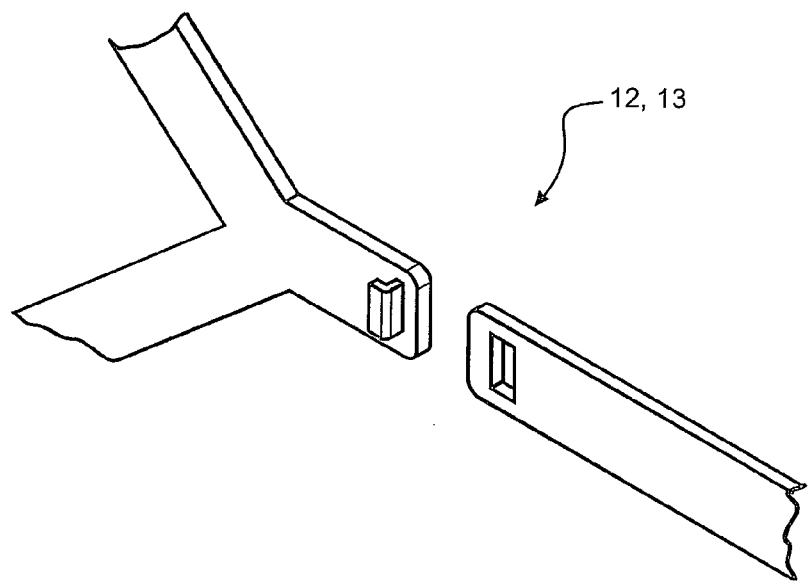
FIGS. 6*a* to 6*g* show different views of two-part connector systems which may be used to connect the headgear and interface.

It will be appreciated that various alternative releasable fastener or releasable type connection systems can be utilised with this invention. In one preferred embodiment, the first connector part or portion 9 can be a hook (or one of a hook or a loop) of a hook and loop type fastener system, and the second connector part or portion 10 would then be the loop (or other of a loop or a hook) for the complementary part of such a hook and loop type fastener system. In the embodiment shown in FIG. 6*g*, both first connector part 9 and second connector part 10 may include a mixture of hook and loop parts. Alternatively, a mushroom-type hook and loop fastener system may be used, as shown in FIG. 6*d*.

Figure 6B:
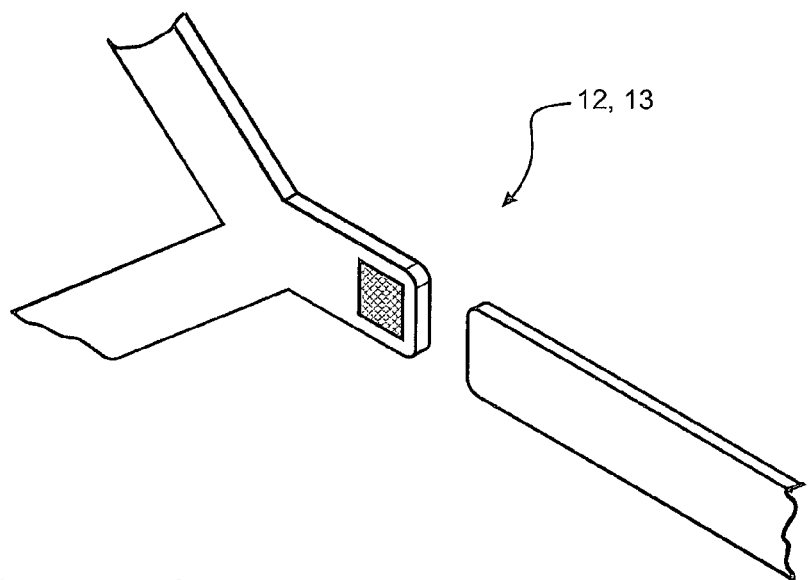

Alternatively, as for example shown in FIG. 6*b*, adhesive parts may be used where those adhesive parts are connectable to, or receivable of, one another. For example, a first part 9 may be an adhesive part, or one part of a two-part adhesive connection system; and, the second part 10 may be a receiver of the first adhesive part, or the part 10 may be the second part of a two-part adhesive system. Such adhesives and parts 9, 10 are provided in a form so as to be releasable from each other.

Figure 6C:
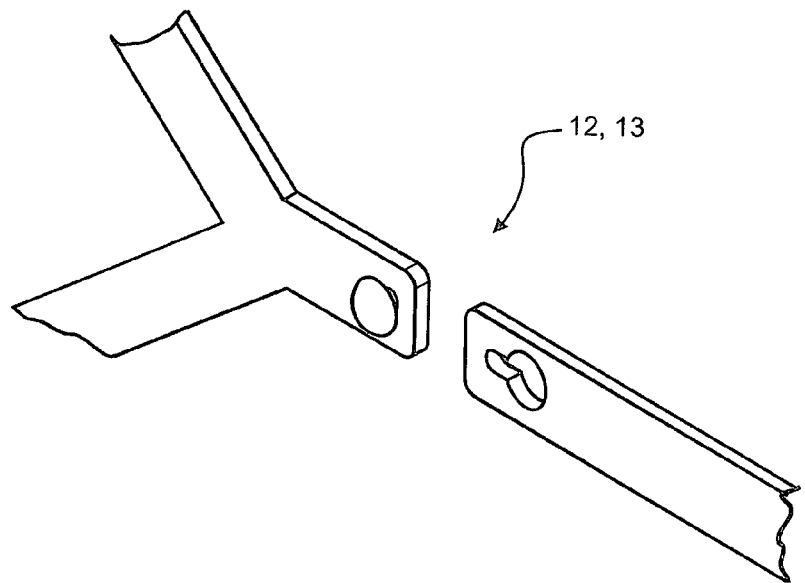
Figure 6D:
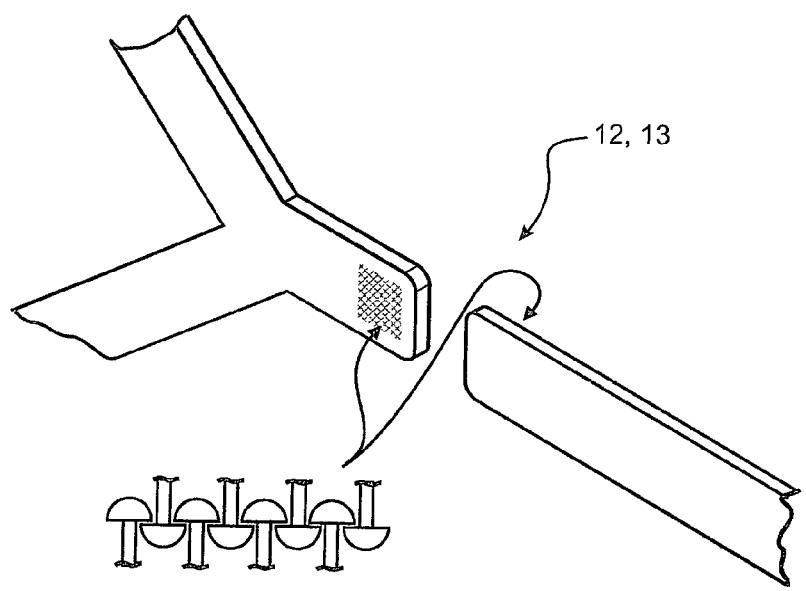
Figure 6E:
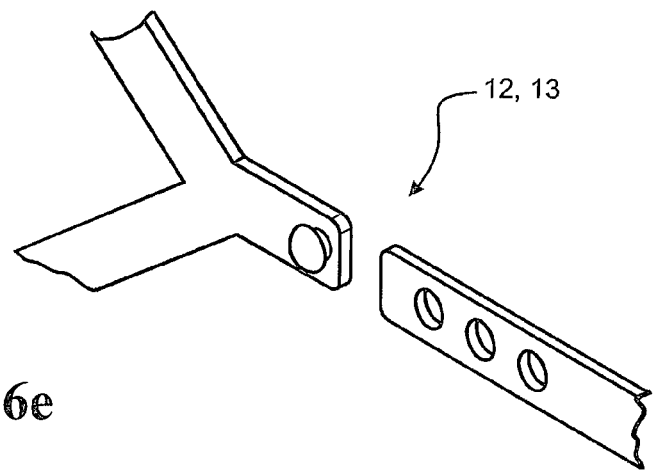
Figure 6F:
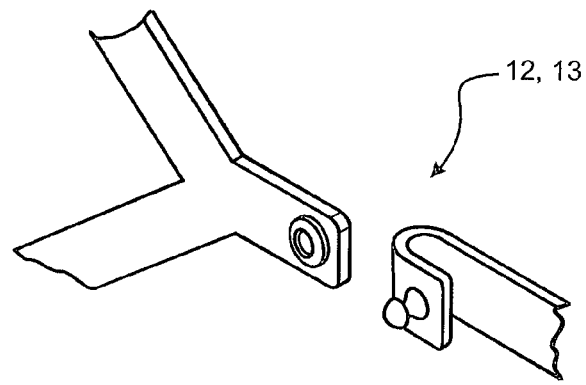
Figure 6G:
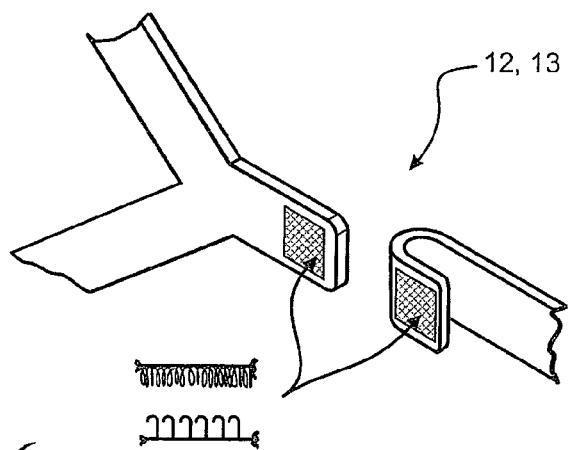

Further examples of releasable connection systems of other embodiments are shown in FIGS. 6*a* to 6*g*. As shown in FIG. 6*a*, first connector part 9 may include an L-shaped retaining hook, which can be inserted into a slot provided in second connector part 10. As shown in FIGS. 6*c* and 6*e*, first connector part 9 may include a dome which is shaped to fit into one or more slots in second connector part 10. The slots may be keyhole-shaped, to prevent accidental removal of the dome from the slot. Alternatively, as shown in FIG. 6*f*, a dome may be provided on second connector part 10, with a complementary receiver on first connector part 9.

FIGS. 6*a*-6*g* illustrates various embodiments of the releasable connection system, including variations of snap-fit or push-fit connection systems.

Advantageously, the releasable connection system utilised is of a substantially similar profile, or substantially similar to the profile of the frame 2. As shown in the figures, the profile is generally a substantially planar or substantially flat profile. This beneficially allows for increased comfort and minimising pressure sores, while minimising the visual impact or obstructions that other headgear of more raised exterior profiles may have or show. Part of the challenge in ensuring compliance with gas delivery systems by infant users is the visual impact that more obtrusive headgear or other systems have on the carers of the user or parents or guardians of infants.

For example, some prior art headgear systems are relatively obtrusive both in their overall size and visual impact. Such obtrusiveness and visual impact can be distressing to the carers or parents of infants undergoing treatment supplied by a user interface. It is therefore an aim of this invention to provide an alternative headgear system which aids in minimising obtrusiveness or visual impact to the carers of infants wearing such headgear, and/or which provides for a headgear and user interface set-up which is easier and less complex that those systems provided previously.

The releasable connection system can be of an interference attachment type system. For example, such an interference attachment system can provide for connection or connectability between a user interface 4 (or a part thereof, or a part connected or attached to a user interface) and the headgear 1, particularly to a region 8 that is either i) extending generally about the ear or ears 7 of the user, or ii) that is extending generally in front of the ear or ears of a user, or iii) at or in front of the ear or ears of a user.

Various types of releasable connection or attachment systems are contemplated. One example is that of a hook and loop type system, other systems may for example include other mechanical quick release systems.

In one preferred embodiment, advantageously, the releasable connection system does not utilise pulley strap systems or buckles. Pulley or buckle type systems can impact on a user's face, particularly an infant face, such as by pressure sores. For example, application of a connection or retention system too tightly on a user's face may contribute to so-called "snub nosing", such as when forces are applied to the nose, septum or philtrum. Such "snub nosing" is to be substantially avoided or reduced. This is uncomfortable for the user (particularly infant users), and distressing for the carer or parents of the infant. Therefore, the use of elasticised or stretchable materials is generally substantially avoided or reduced. For example, the headgear connectable part or portion of the user interface is of a substantially non-elastic part, thereby minimising or reducing the likelihood of any pre-loading of tension build-up between the user interfacing part and the user or user interfacing part and the headgear. At the same time, the user interface is generally maintained in an operational position (e.g. by maintaining the prongs of a nasal cannula in the nares of a user's nose). Then tension or forces between these parts can also be minimised or reduced.

Further, it is desirable for the releasable connection system to be enabled by a quick fit or quick release system or method for ease of installation or removal of the user interface from a user and to the headgear 1. Specifically, this invention reduces the likelihood of the need for application of tension during installation of the user interface to a user in combination with the headgear. Instead, the user interface can be placed into its required user interfacing position, the second connector or part of the user interface is then able to be quickly and relatively easily located upon the region of the headgear 1 adapted to receive the releasable connector region of the user interface. In this manner, a carer or installer of the user interface can, with ease and minimal need for additional help, install a user interface and locate the interface in its required operational position.

This invention beneficially reduces the likelihood of the need for application of adhesive, or adhesive tape, to a user's skin for the installation and placement of a user interface into an operational position. Adhesive tapes or other dermal adhesive patches, particularly for infants, create problems. Problems include, but are not limited to, skin irritation from adhesive chemicals (or adhesive removal chemicals, such as solvents) or tape materials (e.g. due to skin sensitivities), damage to user skin due to repeated application and removal of dermal patches or tapes for positioning or re-positioning of the interface for the user. Re-positioning may be required or adjustments may be needed where treatment therapies are being cycled (i.e. changed from one type of treatment to another, and then back again).

Advantageously therefore, this invention provides for a system of positioning or locating of a user interface for a user, yet reducing the likelihood of the problems associated with adhesive tapes attached to the user's skin.

In positioning of the user interface to the headgear 1, the frame 2 can extend generally about the ears of the user, may partially surround or encircle each, or both, ears, or may wholly surround or encircle the ear or both ears. The figures illustrate one embodiment where the ears are wholly encircled by loops. It will be appreciated that alternative shapes or forms are contemplated.

As more clearly shown by FIGS. 2-5, the headgear 1 can be adjustable. Adjustment allows for fitment to a user's head, such as for improved anatomical adjustment or differing head size.

The headgear 1 can be adjustable for varying the distance the frame 2 extends between the rear region 5 (or region above the nape of a user's neck) and the portion of the frame that extends generally about the ear or ears of a user.

The headgear 1 can alternatively, or in addition, be adjustable for varying the distance the frame extends between the upper region (or top) 6 of a user's head and the portion of the frame that extends generally about the ear of ears of a user.

In another alternative, or combination, the frame 2 extending generally about the ear or ears of a user can be adjustable, for example an adjustment can be made to the size of the loop about an, or each ear of the user. That is, the loop encircling partially or wholly the ear or ears of a user can be made smaller or larger, depending on the head 3 of a headgear user.

The various adjustments above can be made possible by an adjustment strap or straps.

Figure 2:
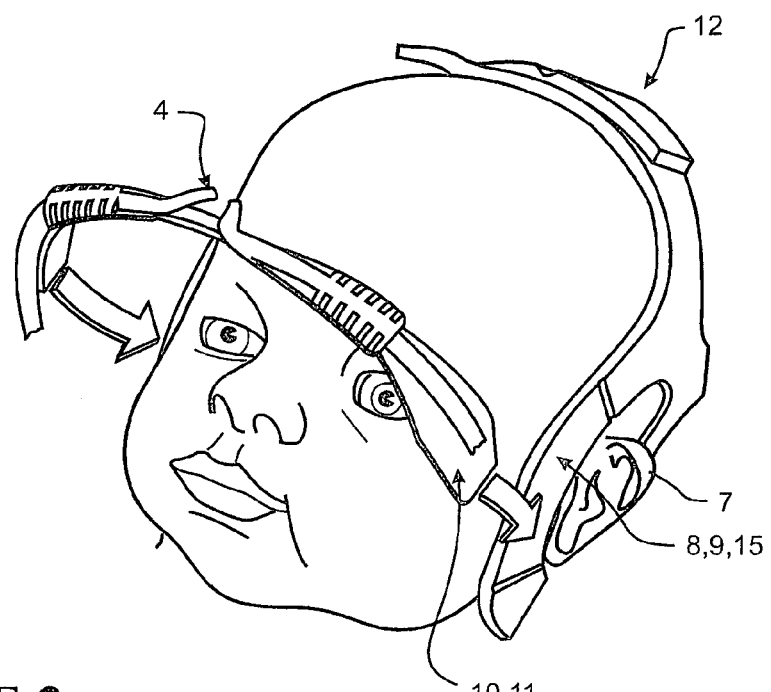
FIG. 2 shows a headgear in position about the head of a user, with a user interface ready to be positioned on a user and be connected to the headgear.
Figure 3:
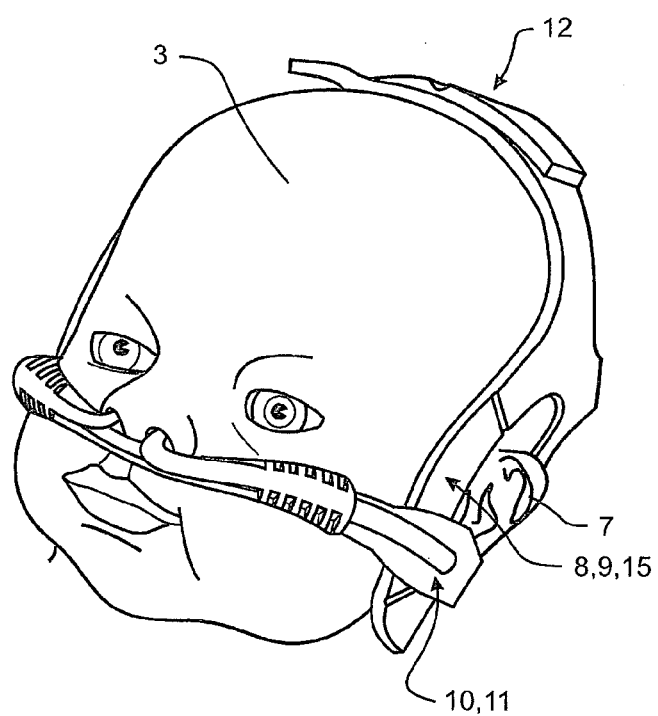
FIG. 3 shows an assembly of the headgear and user interface subsequent to interface positioning and connection of the interface with the headgear.
Figure 4:
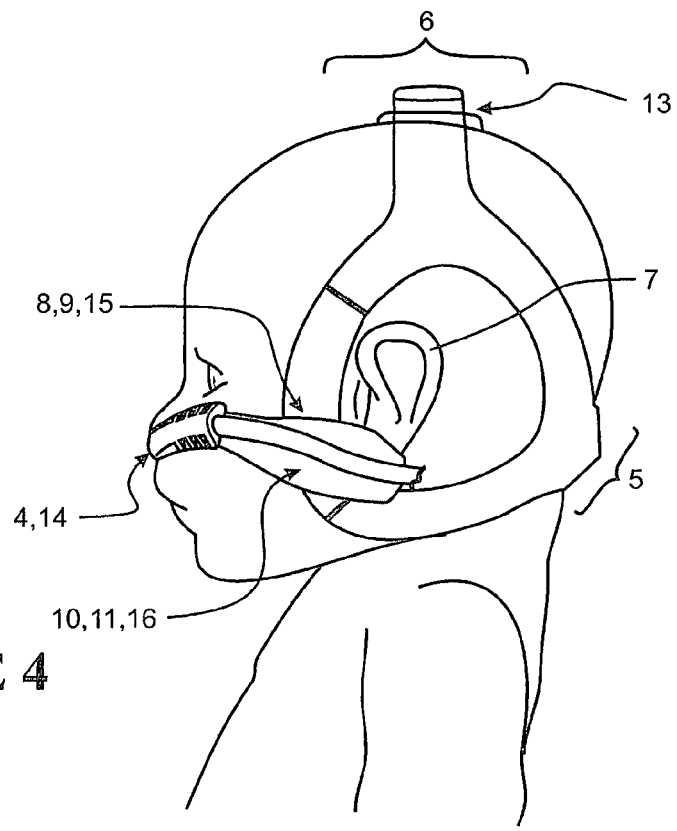
FIG. 4 shows a headgear with a user interface assembly in connection, demonstrated is connection of the interface to the headgear on a region of headgear in front of the ears of the user.
Figure 5:
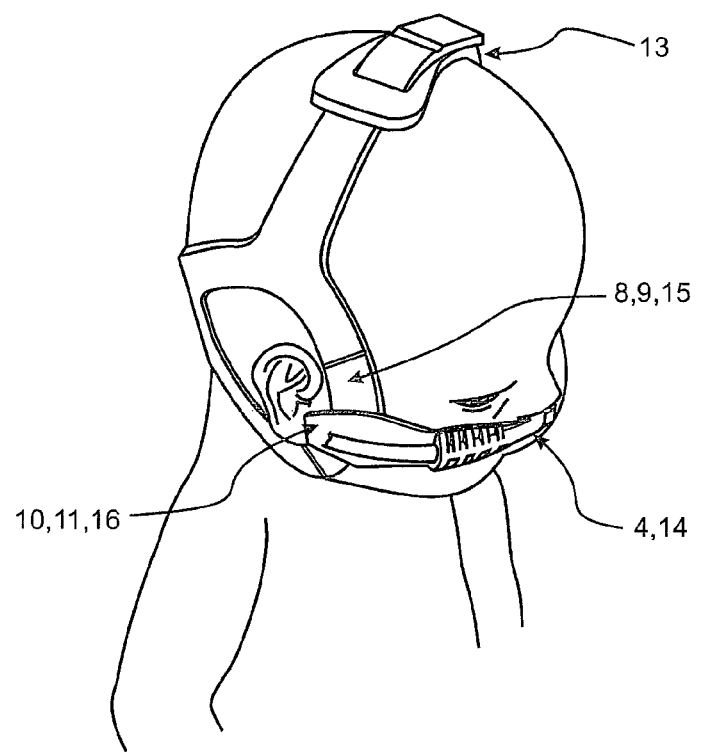
FIG. 5 shows a different view of the headgear and interface assembly of FIG. 4.

In one form, the adjustment strap or one of the adjustment straps may be that indicated by numeral 12 as being a part of the frame positionable generally about the upper region (or top) 6 of the user's head. Strap 12 is shown in FIGS. 2 and 3 as components that have reciprocal ones of a two-part releasable connection system, such as hook and loop components. Alternatively, FIGS. 4 and 5 illustrate an adjustment strap 13 in the form of a buckle arrangement where one of the adjustable straps is insertable through the buckle and positionable, again for example by use of a releasable connection system, such as that of a hook and loop type system being provided on an underside of the strap and connectable with an outward facing side of the buckle side of the strap.

Similar adjustment strap systems can be utilised for an adjustment strap or straps that are a part of the frame 2 and positionable generally about the rear region (or region above the nape of the user's neck) 5.

Such adjustment straps can be both a part of the frame 2 and positionable generally about the upper region (or top) 6 of the user's head and the frame positionable generally about the rear region (or region above the nape of the user's neck) 5. Optionally, included can be adjustment around the ear region.

With respect to the head 3 of the user, the rear region 5 is generally a lower rear region of the user's head, or generally the region above the nape of the user's neck. The upper region 6 is generally a region about the top of a user's head.

In the headgear 1 may comprise a semi-rigid frame engageable with the head of a user, the frame extending generally about a rear region of a user's head and generally about an ear or both ears of a user's and wherein the frame further comprises a releasable connection system for releasable connection with a user interface.

In another embodiment, the frame 2 can be a one-piece or a single part article or is a unitary piece of headgear. For example, the frame 2 is not provided by multiple parts that must be each assembled or connected together to provide the semi-rigid headgear.

In another embodiment, the frame 2 can be assembled into a headgear 1 which is semi-rigid, and being effectively a unitary piece of headgear, except for any optional adjustment straps. Optionally, the frame can be formed of all the same material.

Being of a semi-rigid form, it will be appreciated the frame 2 has an interface 4 which may be releasably connected thereto. Such self-supporting form of the headgear 1 allows for a distribution of any force applied to the headgear 1 from positioning of the interface. Such semi-rigid headgear 1 provides a frame 2 about which a user interface can be releasable connected thereto, and into which the head 3 of a user can be inserted.

In another exemplar, the semi-rigid frame can be formed of or from a substantially non-elastic construction or substantially non-elastic material. In this manner, the frame 2 is formed or constructed so as to be of a substantially self-supporting shape or configuration. In this manner, the frame provides a substantially self-supporting frame 2 to which a user interface 4 (or a part thereof, or a part connected or attached to a user interface) is connectable and supported in-situ therefrom.

The headgear 1 may be constructed to have the frame 2 being of a substantially planar or substantially flat profile. Such profile can allow for less bulky or obtrusive headgear, or can allow for wider distribution of any forces about a user's head. The flat or planar profile may contribute or allow for larger contouring of headgear 1 surface about the user's head 3. Similarly, the releasable connection system components are preferably of low profile for similar reasoning and reduced bulkiness.

The frame can be constructed or manufactured from various materials. Materials of a smooth surface or comfortable or soft outer material disposition for user may be preferred. Included are those materials of dermatological sensitivity.

In one embodiment, the headgear 1 can be constructed from non-woven materials, or those polymers providing suitable semi-rigidity. Other examples include forming of the frame from thermoplastic or thermosetting polymeric materials, or composites therefrom. Alternatively, the frame may be formed of or from a weldable polymeric material. Woven materials that do not fray easily, but which provide suitable semi-rigidity, may also be used.

Polyethylene terephthalate (PET), polyethylene (PE), or polyesters are other contemplated materials which may be formed into a suitably shaped frame 2. Similarly, the frame 2 may be formed from a non-woven polyethylene terephthalate (PET)/polyethylene (PE) laminated composite, or a non-woven PET/polyester laminated composite. Other laminate composites are also contemplated; suitable are those which provide for a level of semi-rigidity.

Figure 7:
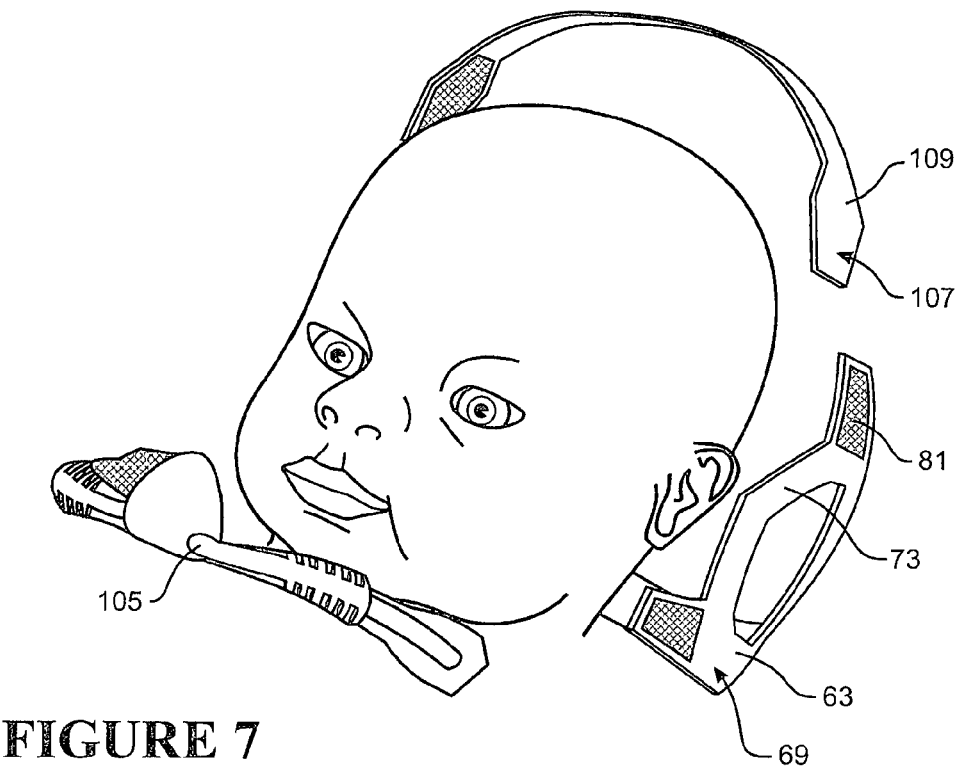
FIG. 7 is an exploded view showing the relative location of components of the headgear and interface of FIG. 6.
Figure 8:
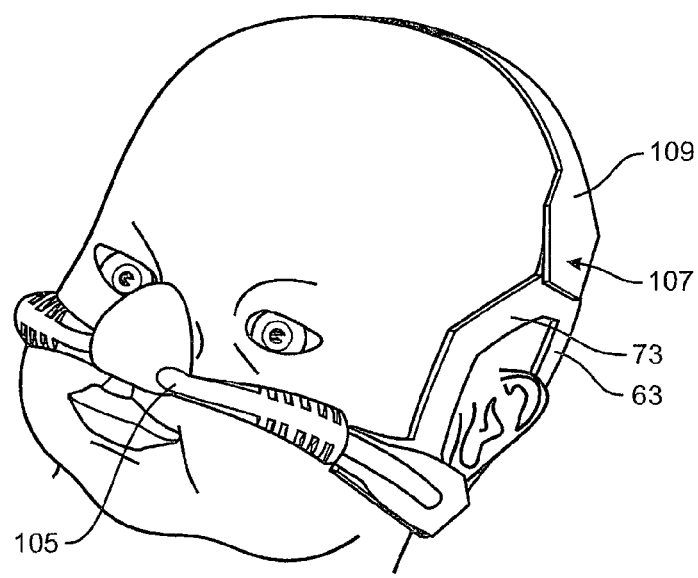
FIG. 8 shows the user wearing the headgear and interface viewed from in front and to one side.
Figure 9:
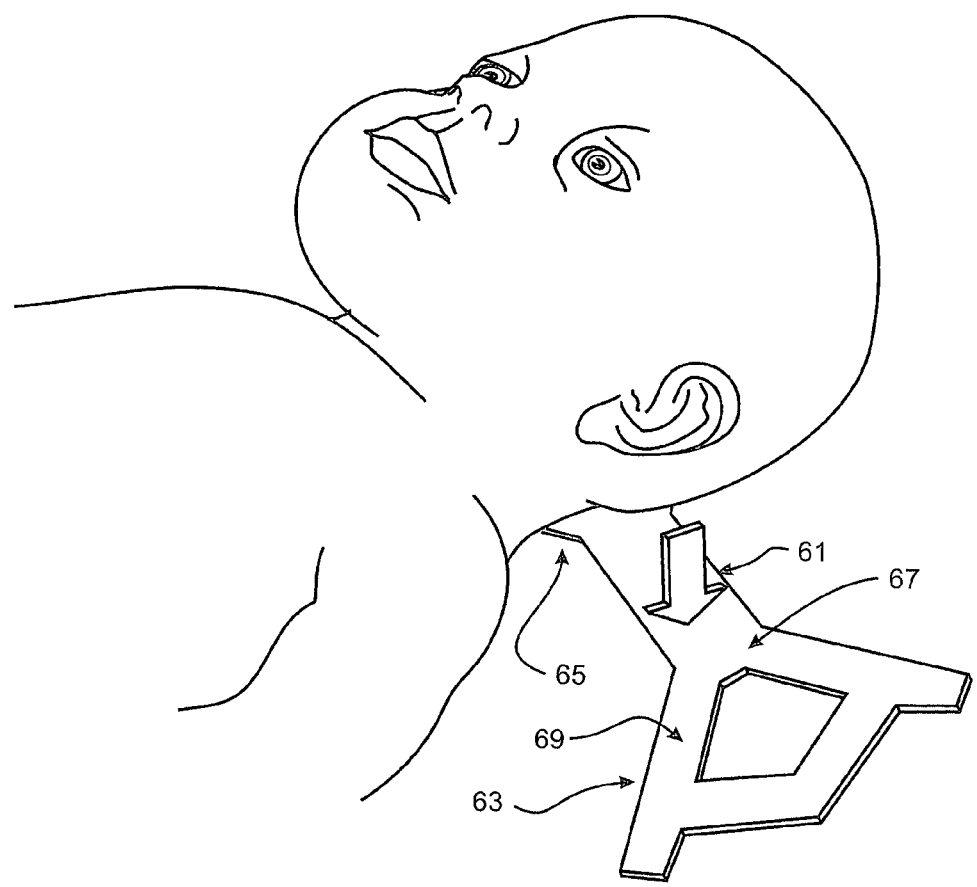
FIG. 9 shows a component of headgear of FIGS. 6 to 8 laid flat for receiving the head of the user.
Figure 10:
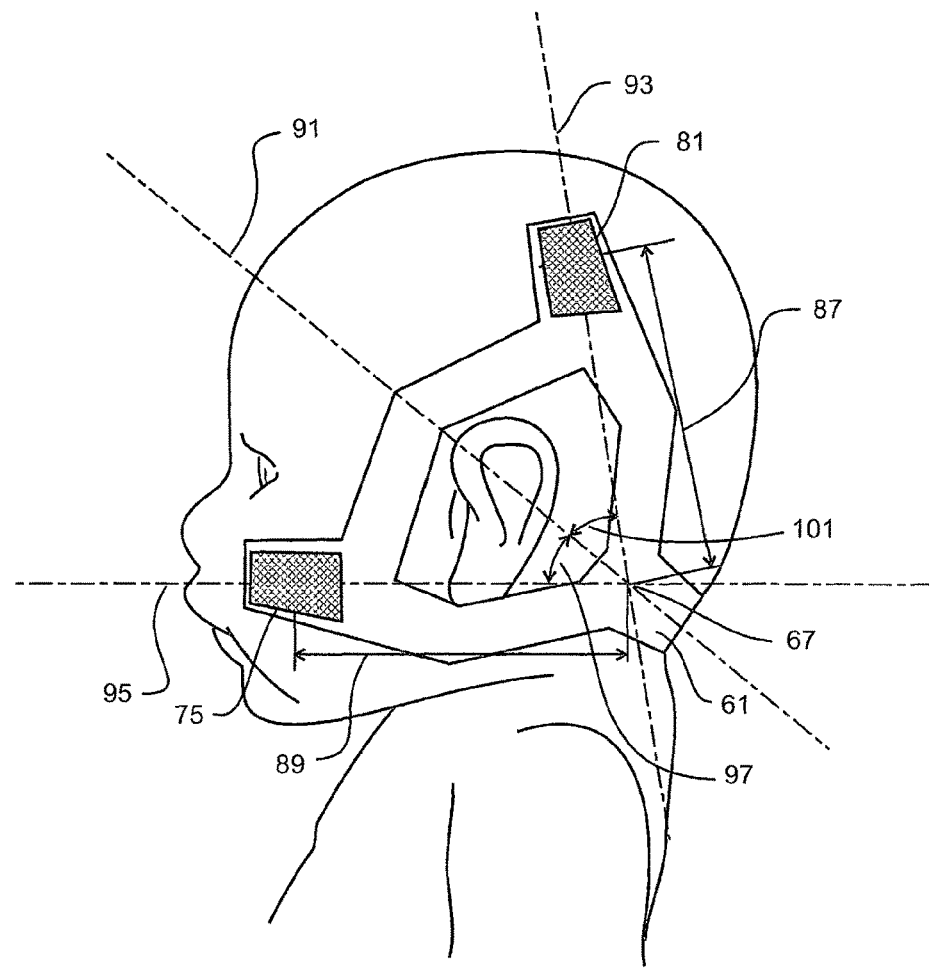
FIG. 10 is a profile view showing the headgear components of FIGS. 6 to 8 wrapped up the sides of the head of the user, prior to attaching additional components and the interface.

Another embodiment is illustrated in FIGS. 6 to 10. The headgear and interface assembly as illustrated in FIGS. 6 to 8 with references to its position and fit on the user. FIGS. 9 and 10 illustrate the form and fit of the primary headgear component. The primary headgear component comprises a backstrap 61 that extends around the back of the head of the user below the occipital protuberance. A first ear loop 63 extends from one end of the backstrap. A second ear loop 65 extends from the other end of the back strap 61. Each of the ear loops is of similar form. In some embodiments, the ear loops are symmetric across the sagittal plane. That is, the first ear loop is a mirror image of the second ear loop considered relative to a reference plane bisecting the backstrap. In some embodiments, the first and second ear loops are identical. In these embodiments, the shape of the ear loops and the angle of the ear loops relative to the ends of the backstrap and the shape of the backstrap are such that the headgear, when laid flat, is rotationally symmetric when rotated through an angle of 180°.

In respect of the various planes of symmetry of the headgear component 61, the first and second plane may be substantially mutually perpendicular to one another. The first plane corresponding to the sagittal plane of the user, for example the left ear strap can be substantially a mirror image of the right ear strap. The second plane corresponding to the transverse plane of the user, for example when the headgear is cut lengthwise along the length of the backstrap, the top half can be substantially a mirror image of the bottom half. Yet further, the headgear component 61 can be symmetrical about a third plane corresponding to the coronal plane of the user, for example the front face or side is the mirror image of the back face or side.

In other embodiments, they may be sufficiently physically similar to be functionally identical without being physically identical. Each ear loop is connected to the backstrap 61 at a connecting portion 67. The ear loop diverges form the connecting portion 67 such that one arm 69 of the ear loop projects forward and below the ear, and the other arm 71 of the ear loop projects upward behind the ear. A third arm 73 of the ear loop extends generally upward in front of the ear and upward and rearward above the ear. The arms 69, 71 and 73 may in some embodiments comprise a series of straight portions.

In other embodiments, the arms 69, 71 and 73, or one or more of the arms, comprise smooth curves. In some embodiments, the edges of the arms comprise combinations of straight sections and smooth curves. The arms 69, 71 and 73 define between them an ear opening 75. The limits of the ear opening 75 are defined by the inward edges of each of the arms 69, 71 and 73. At the junction of first arm 69 and third arm 73, the ear loop includes a first connections zone 75. In some embodiments, the connection zone 75 is substantially on the junction 77. In other embodiments, the connection zone 75 is located on an extended tab 79 extending from the junction 77.

In some embodiments, the extended tab 79 extends from the ear loop 63 in a direction such that it appears an extension of the first arm 69.

The first connection zone provides an area for connection of a portion of an interface to the headgear. This area may include portions or parts of a fastener or connection system. For example, the area may include one part of a two-part connection system such as either the hook or loop components of a hook and look fastener system. Alternatively, the area may include a receptive surface for connection of an adhesive fastener system, such as a smooth plastic surface. Alternatively, the area may include a clip component for connecting with a clip component of an interface. The ear loop 63 includes a second connection zone at or adjacent the connection zone 81 at or adjacent the junction 83 between the second arm 71 and the third arm 73. In some embodiments, the connection zone 81 may be located on a tab 85 extending from the junction 83. In some embodiments, the tab 85 extends from the junction 83 so as to be substantially an extension of the line of the second arm 71. The connection zone 81, like the connection zone 75 includes provision for securing other components to this primary headgear component.

According to one feature of this headgear, each of the connection zones 75 and 81 are configured to be substantially interchangeable and thus to connect one of an interface component and a headgear component. That is, connection zone 75 can receive either a headgear component and an interface component, and connection zone 81 can receive either of an interface component and a headgear component.

In some embodiments, the distance between the region 67 where the ear loop 63 connects to headgear backstrap 61 and connection zone 75 is the same as the distance between the region 67 and connection zone 81. This is best illustrated in FIG. 10 by a comparison of distance 89 and distance 87. The direction from region 67 and first connection zone 75 extends at an angle 97 relative to a centerline direction 91 of the backstrap 61. The line 93 between region 67 and connection zone 81 extends at an angle 101 to the centerline 91. In some embodiments, the angle 97 and the angle 101 are substantially equal. By substantially equal, we mean within 10 degrees, within 5 degrees or within 3 degrees or less.

With the primary headgear component fitted to the head of the user, one of the connection zones of the ear loop 63 is presented low down in front of the ear of the user and presents generally forwards. The other of the connection zones is located high up above and behind the ear of the user and presents generally upwards. The forward lower down connection zone is placed on the cheeks of the user, and can receive a connecting portion 103 of a user interface 105. The connecting zone above the ear can receive a connecting portion 107 of an upper head strap 109.

In some embodiments, the connecting portion 103 of interface 105 includes a second part of a two-part connection system adapted to engage the first part provided at the respective connection zones of the primary headgear component. Similarly, the connecting portion 107 of head strap 109 includes a second part of the connection system, also to connect with the other part of the fastener system that is provided on the connection zones of the primary part of the headgear. The two-part connection systems as described previously with respect to headgear 1 apply with respect to the connection zones of the headgear component 61.

It is to be additionally noted that in another embodiment a snap-fit or snap-dome type connection may be used a two-part connection system.

According to these embodiments, the headgear is rotationally functionally symmetric so that whichever way round the headgear is placed on the head of the user, each of the ear loops will accommodate the ear of the user with the connection zones presented at the same locations on the head of the user. The connection zones are also interchangeable so that the top strap 109 may connect to whichever connection zone results at the upper portion of the head and the interface 105 may be connected to whichever connection zone results in front of the ear.

One aspect of this symmetricity and functional accommodation of different headgear orientations arises in the shape of the ear loop 63 and in particular, the shape of the ear opening defined by the inner edges of the arms 69, 71 and 73.

The first arm 69 of each ear loop is concave toward the ear. In some embodiments, the second arm 71 of each ear loop is concave toward the ear.

In some embodiments, the front ear loop arm 73 is concave toward the ear.

In some embodiments, the primary headgear component may include connection zones on both sides of the web of material from which it is constructed at or adjacent the junctions 77. In these embodiments, the headgear may be functionally reversible as well as functionally rotationally symmetric. In these embodiments, it is not possible for a user correctly placing the backstrap behind the head of the wearer as illustrated in FIG. 9 and bringing the ear loops up the sides of the head of the wearer as illustrated in FIG. 10 to find that they had not oriented correctly to receive the user interface and top strap.

The backstrap 61 may optionally additionally comprise one or more rigidising members 120. Such members being configured to allow the backstrap 61, and therefore at least part of the headgear, to at least partially retain its shape when it is bent around a patient's head, thereby making it easier, for example for a single user, to attach an interface and/or top strap and/or to fit the backstrap 61 about a patient's head. Such members 120 may preferably be disposed or embedded in or upon the backstrap 61, and may be in a manner so that such members 120 do not directly contact the user. Alternatively, such members 120 may be provided in a non-embedded configuration, but where at least such a member 120 is covered or protected so as to not be in direct contact with the user.

In various embodiments, such rigidising member or members 120 may be formed or comprise of any suitable material or constituent material able to facilitate the retention of a shape. For example, such rigidising member 120 may be formed of one or more of: a copper piece, a copper wire or strap or length, an aluminium piece, an aluminium wire or strap or length, a ductile plastic piece and/or a ductile plastic wire or strap or length.

Figure 11:
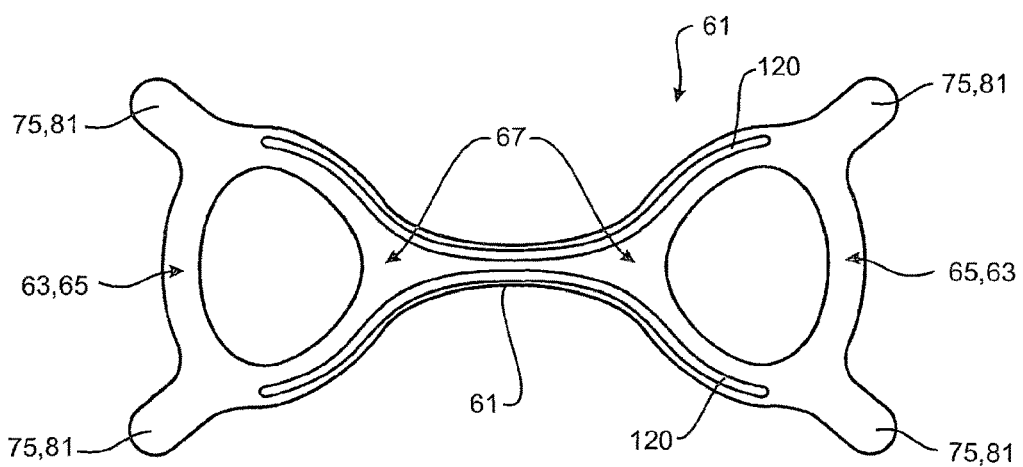
FIG. 11 shows a headgear component including a pair of rigidising members.

FIG. 11 illustrates one example of a backstrap 61 with a pair of rigidising members 120 disposed within the backstrap 61.

It will be appreciated the rigidising member may itself be of a continuous or discontinuous length. For example, in one such embodiment the rigidising member may comprise a series of discrete sections or a plurality of rigidising member components disposed of or embedded in or upon the backstrap 61. Such discrete component sections themselves form a rigidising member 120. In yet another such embodiment, the rigidising member may be single length or a single component, for example the whole length of a rigidising member can be of a rigidising material or component.

The backstrap 61 forms a headgear component that can be one part or component of a headgear for a user.

Particularly suited to this invention is the headgear, or user interface, or both, for infant use. Particularly this is due to their head size, need for delicate application of user interfaces or headgear with minimal disturbance to the infant, and desire to improve the ease of fitment of user interfaces to infants without the need for the more complicated systems currently available.

Such user interfaces are desirably those connectable to gas delivery systems for various breathing gas treatments, e.g. CPAP or other breathing gas treatments. User interfaces are any of those suitable as gas delivery devices, particularly those of masks, nasal cannula, or other oronasal devices.

In respect of a further embodiment there is provided a user interface 4. Such a user interface 4 comprises a user interfacing part or portion 14, and a headgear connectable part or portion 16.

In another embodiment however, there is provided the user interface 4 comprising the user interfacing part or portion 14, and a headgear connection system part or portion 16 for releasable connection with a releasable connectable part or portion 15. The headgear connection system may be provided by, or on, a region of (or in attachment or connection with) the user interface. In this manner, a part of the user interface or part that may be connected to the user interface part 16 may be supported by the releasable connection system part or portion 15 of the headgear. See for example FIGS. 2-5 in which the interface 14 is supported or attached to the portion 15. In some embodiments, interface 14 may be provided with one or a pair (or more) of parts or portions 16 connectable with the headgear, which parts or portions 16 may extend from interface 14 for connection with the headgear. In some embodiments, the releasable connectable part or portion 15 may be integral with the user interfacing part or portion 16 or may be over-moulded with the user interfacing part or portion 16.

The headgear connection system or its part or portion 16 can be in the form of a backing or a substrate to which the user interface is attached or connected or connectable thereto. Such a backing or substrate can extend across the whole back or skin-side of the user interface, or it may be attached or connected (or otherwise formed with) outer peripheral edges or sides of the user interface which then extend sufficient length to be enabled to releasably connect with the headgear 1 connectable part 15, for example on region 8.

Such part or portion 16 of the interface 4 is capable of supporting sufficient shear and pull forces exerted by positioning of the user interface and connecting of the part or portion 16 with the headgear 1 region 8. Sufficient connection strength or resistance is advantageously provided to limit or reduce the likelihood of an infant removing the part or portion 16 of the interface 4 from the headgear 1.

Desirably, suitable materials for such part or portion 16 are one or more of: dermatological appropriate/safe for skin contact (particularly for infant skin), smooth surfaced (to reduce or minimise abrasion to a user's skin), generally of a flat or planar profile (i.e. visually less obtrusive), and may be of a soft outer-most surface for improved feel to a user or carer or parent. Ideally, such materials may not produce lint, or be easily pilled, or easily frayable. Preferred materials also include those which allow for ease of cleaning.

The figures show the gas delivery tube connected to the user interface 4, 14. The gas delivery tube or any other tubes that may be connected to a user interface are optionally able to be freely positioned. Such tubes are not attached to the part 10 of the interface. The ability to independently position such tubes allows the carer (e.g. nurse) to arrange the tube or tubes in a manner most comfortable for the user to reduce the likelihood of pressure sores or other discomforts and reduce the likelihood of tubular kinking or other such situations.

As with the headgear 1, the headgear connection system part or portion 16 of the interface forms one (or a first) part of a two-part connection system. The other, or another, of the two-part connection system is then provided by the frame 2 (or headgear 1) as previously defined above. For example, one part can be one of a hook or a loop (of a hook and loop type releasable connection system), while the other part can the other of a loop or a hook, being the reciprocal connection part of such a hook and loop type system.

Such a headgear connection system part or portion of the user interface can be for example those which are an interference attachment system where a first part is interferingly attachable or connectable to a second part. Connection or connectability is desirably between the user interface (or a part thereof, or a part connected or attached to a user interface) and a headgear (as that defined above), such as on or at one or more of: a headgear region extending generally about the ear or ears of a user; a headgear region extending generally in front of the ear or ears of a user; a headgear region at or in front of the ear or ears of a user.

Such headgear connection system part or portion 16 can be a strip or a strap or a length of a connector part of the connection system. Such strip or strap or length extends about or from around the user interface 14 to be connectable to or on or about a region of a frame, the frame (or headgear) as defined above. The releasable connection system part or potion 16 can be a flexible, yet non-elasticised part. In this manner, the portion 16 can be attached or connected to the frame 2 about for example region 8, 15, whilst not being overly stretchable, and therefore imparting tension forces to the user (particularly for reducing the likelihood of "snub nosing" problems).

In one preferred embodiment, advantageously, the releasable connection system does not utilise pulley strap systems or buckles. Pulley or buckle type systems can impact on a user's face, particularly an infant face. For example, application of a connection or retention system too tightly on a user's face may contribute to so-called "snub nosing", such as when forces are applied to the nose, septum or philtrum.

Beneficially the releasable connection system enables connection between a user interface and the headgear 1, whilst reducing the likelihood of the application of tension during installation of the user interface to a user in combination with the headgear.

A first connector portion 9 is provided by, or on, a region of headgear (as defined above), and a second connector portion 10 is provided by, or on, a region of (or in attachment or connection with) the user interface.

Again, with respect to the user interface, the user interface releasable connection system part or portion is advantageously of a substantially low profile, for example it may be a substantially similar profile to the profile of the frame (e.g. planar or flat).

The user interface may be any of those options mentioned previously above. In this invention, particularly preferred are user interface options for use with infants. Interfaces are connected to or connectable to gas delivery systems, especially breathable gas systems, and to other parts of a breathing system or medical circuit.

An assembly of the headgear 1 and user interface 4 provides for a system of improving comfort of a user and for aiming to improve compliance of treatment from user interfaces and gas delivery systems. In a further embodiment therefore, there is provided an assembly comprising a headgear 1, the headgear being as previously defined above. The assembly also comprises a user interface 4, the user interface being as previously defined above. The headgear 1 and user interface 4 are releasably connectable to each other.

As mentioned above, the headgear 1 is supportive or supporting of the user interface 4 in an interface 4 in-situ or installed in-use (or operational) position with or on a user. The headgear 1 is provided with a first or one part of a two-part releasable connection system, and the user interface 4, 14 or a region 16 of (or in attachment or connection with) the user interface comprises a second or other of the two-part releasable connection system. Such a system allows for the releasable retaining of the interface 4, 14 on a user.

The foregoing description of the invention includes preferred forms thereof. Modifications may be made thereto without departing from the scope of the invention.

The invention claimed is:

1. A headgear component as a part of a headgear for a respiratory device comprising:
   a backstrap,
   a first ear loop extending from one end of the backstrap, the first ear loop following a path defining a first ear through opening,
   a second ear loop extending from another end of the backstrap, the second ear loop following a path defining a second ear through opening,
   a first pair of connection zones on the first ear loop, each connection zone of the first pair of connection zones spaced an equal distance from the backstrap and spaced from each other,
   a second pair of connection zones on the second ear loop, each connection zone of the second pair of connection zones spaced an equal distance apart from the backstrap and spaced from each other, a first connection zone of the first pair and a first connection zone of the second pair are toward a first side of the backstrap, and a second connection zone of the first pair and a second connection zone of the second pair are toward a second side of the backstrap, wherein the headgear component when laid flat for receiving a head of a user is symmetrical along a first plane and a second plane.

2. The headgear component as claimed in claim 1, wherein the backstrap is adapted to cross behind the head of the user, below the occiput or occipital bone.

3. The headgear component as claimed in claim 1, wherein the first plane is parallel to the sagittal plane of the user when the headgear is laid flat for receiving the head of the user, and the second plane is parallel to the transverse plane of the user when the headgear is laid flat for receiving the head of the user.

4. The headgear component as claimed in claim 1, wherein the headgear component is symmetrical along a third plane.

5. The headgear component as claimed in claim 4, wherein the third plane is parallel to the coronal plane of the user when the headgear is laid flat for receiving the head of the user.

6. The headgear component as claimed in claim 1, wherein the headgear component is symmetrical about the backstrap.

7. The headgear component as claimed in claim 1, wherein each ear loop comprises projecting portions, and the connection zones are located on the projecting portions.

8. The headgear component as claimed in claim 1, wherein the headgear component comprises a flat web of a material, the web being bendable.

9. The headgear component as claimed in claim 1, wherein the headgear component is reversible so that each face is configured to comfortably contact the user, and wherein the connection zones are provided on both faces of the headgear component.

10. The headgear component as claimed in claim 1, wherein the headgear component comprises a flat web of a material, and each connection zone includes a component of a releasable fastening system on both the first and second sides of the web of material.

11. The headgear component as claimed in claim 1, wherein a top strap comprising a first end and second end, wherein the first end is configured to be releasably fastened to one of the first pair of connection zones presented outwardly, and the second end is configured to be releasably fastened to one of the second pair of connection zones presented outwardly, the top strap extending substantially across an upper region or top of the user's head.

12. The headgear component as claimed in claim 1, including one or more rigidising members in one or more of the backstrap, the ear loop or the top strap.

13. The headgear component as claimed in claim 12, wherein said rigidising member comprises one or more of copper wire, a copper piece or strap or strip, aluminium wire, aluminium piece or strap or strip, ductile or conformable plastics.

14. The headgear component as claimed in claim 1, wherein the shapes and relative positioning of the backstrap, the ear loops, and the connection zones, being such that
   in a first mode of use, the backstrap crosses behind the head below the occiput or occipital bone, an ear loop is disposed around each ear, the connection zones toward the first side of the backstrap presenting outwardly from the user's head, and the connection zones toward the second side of the backstrap presenting inwardly toward the user's head, and in a second mode of use, the backstrap crosses behind the head below the occiput or occipital bone, an ear loop is disposed around each ear, the connection zones toward the second side of the backstrap presenting outwardly from the user's head, and the connection zones toward the first side of the backstrap presenting inwardly toward the user's head.

15. The headgear component as claimed in claim 1, wherein one pair of the connection zones forms in use, a releasable connection system for releasable connection with a user interface, and wherein the releasable connection system is a two-part connector system.

16. The headgear component as claimed in claim 15, wherein a first connector part or portion of the two-part connector system is one of a hook or a loop of a hook and loop type fastener system, and a second connector part or portion of the two-part connector system is the other of a loop or a hook for the hook and loop type fastener system.

17. The headgear component: as claimed in claim 15, wherein the releasable connection system is of a substantially planar or flat profile, the flat or planar profile contoured for planar or flat contact with the user's head.

18. The headgear component as claimed in claim 1, wherein the headgear component is a provided as one-piece or as a single part article or is a unitary piece of headgear.

19. The headgear component as claimed in claim 18, wherein the component forms a part of a semi-rigid headgear frame.

20. The headgear component as claimed in claim 1, wherein the headgear is adjustable at a portion that contacts an upper region of the user's head.

* * * * *

UNITED STATES PATENT AND TRADEMARK OFFICE
CERTIFICATE OF CORRECTION

PATENT NO. : 10,463,826 B2
APPLICATION NO. : 14/401446
DATED : November 5, 2019
INVENTOR(S) : Laurence Gulliver et al.

Page 1 of 1

It is certified that error appears in the above-identified patent and that said Letters Patent is hereby corrected as shown below:

In the Specification

In Column 15, Line 1, delete "back strap" and insert --backstrap--.

In the Claims

In Column 22, Line 13 (Approx.), Claim 17, delete "component:" and insert --component--.

Signed and Sealed this
Seventeenth Day of March, 2020

Andrei Iancu
*Director of the United States Patent and Trademark Office*